(12) United States Patent
Wahlstrand et al.

(10) Patent No.: US 7,174,219 B2
(45) Date of Patent: Feb. 6, 2007

(54) LEAD ELECTRODE FOR USE IN AN MRI-SAFE IMPLANTABLE MEDICAL DEVICE

(75) Inventors: Carl D. Wahlstrand, Lino Lakes, MN (US); Thomas Barry Hoegh, Edina, MN (US); Gregory A. Hrdlicka, Plymouth, MN (US); Thomas E. Cross, Jr., St. Francis, MN (US); James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 234 days.

(21) Appl. No.: 10/981,092

(22) Filed: Nov. 3, 2004

(65) Prior Publication Data

US 2005/0222647 A1  Oct. 6, 2005

Related U.S. Application Data

(60) Provisional application No. 60/557,991, filed on Mar. 30, 2004.

(51) Int. Cl.
*A61N 1/05* (2006.01)
(52) U.S. Cl. .................. 607/116; 600/373
(58) Field of Classification Search ............. 607/116, 607/119, 122, 63; 600/373, 374; 128/901
See application file for complete search history.

(56) References Cited

U.S. PATENT DOCUMENTS

| | | | |
|---|---|---|---|
| 3,788,329 A | 1/1974 | Friedman | |
| 3,915,174 A | 10/1975 | Preston | |
| 4,038,990 A | 8/1977 | Thompson | |
| 4,220,813 A | 9/1980 | Kyle | |
| 4,280,507 A | 7/1981 | Rosenberg | |
| 4,320,763 A | 3/1982 | Money | |
| 4,628,942 A | 12/1986 | Sweeney et al. | |

(Continued)

FOREIGN PATENT DOCUMENTS

EP  0 713 714 A3  5/1996

(Continued)

OTHER PUBLICATIONS

Baker, K. et al.; "Neurostimulation Sytems: Assessment of Magnetic Field Interactions, Associated with 1.5- and 3-Tesla MR Systems" :, 2004 Annual Meeting of the Int'l Soci . . . .

(Continued)

*Primary Examiner*—Robert E. Pezzuto
*Assistant Examiner*—Eric D. Bertram
(74) *Attorney, Agent, or Firm*—Ingrassia, Fisher & Lorenz, P.C.

(57) ABSTRACT

A pulse stimulation system configured for implantation into a patient's body comprises a pulse stimulator, a conductive stimulation lead having a proximal end electrically coupled to the pulse simulator and having a distal end, and an electrode assembly coupled to the distal end of the stimulation lead. The electrode assembly comprises an electrode body having a therapy electrode thereon that is electrically coupled to the stimulation lead for delivering therapy to the patient. A floating electrode is configured to contact the patient's body tissue and has a surface area substantially larger than that of the therapy electrode. A filter is coupled between the therapy electrode and the floating electrode for diverting RF energy toward the floating electrode and away from the therapy electrode.

61 Claims, 9 Drawing Sheets

U.S. PATENT DOCUMENTS

| | | |
|---|---|---|
| 4,726,379 A | 2/1988 | Altman et al. |
| 4,852,585 A | 8/1989 | Heath et al. |
| 4,920,980 A | 5/1990 | Jackowski |
| 4,947,866 A | 8/1990 | Lessar et al. |
| 4,951,672 A | 8/1990 | Buchwald et al. |
| 4,991,583 A | 2/1991 | Silvian |
| 5,018,523 A | 5/1991 | Bach, Jr. et al. |
| 5,020,544 A | 6/1991 | Dahl et al. |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,217,010 A * | 6/1993 | Tsitlik et al. ............... 607/9 |
| 5,314,459 A | 5/1994 | Swanson et al. |
| 5,323,776 A | 6/1994 | Blakeley et al. |
| 5,335,657 A | 8/1994 | Terry, Jr. et al. |
| 5,366,496 A | 11/1994 | Dahl et al. |
| 5,370,644 A | 12/1994 | Langberg |
| 5,417,719 A * | 5/1995 | Hull et al. ............... 607/46 |
| 5,458,629 A | 10/1995 | Baudino et al. |
| 5,476,496 A | 12/1995 | Strandberg et al. |
| 5,515,848 A | 5/1996 | Corbett, III et al. |
| 5,523,578 A | 6/1996 | Herskovic |
| 5,591,218 A | 1/1997 | Jacobson |
| 5,629,622 A | 5/1997 | Scampini |
| 5,649,965 A | 7/1997 | Pons et al. |
| 5,683,435 A | 11/1997 | Truex et al. |
| 5,697,909 A | 12/1997 | Eggers et al. |
| 5,697,958 A | 12/1997 | Paul et al. |
| 5,702,437 A | 12/1997 | Baudino |
| 5,722,998 A | 3/1998 | Prutchi et al. |
| 5,727,552 A | 3/1998 | Ryan |
| 5,751,539 A | 5/1998 | Stevenson et al. |
| 5,782,241 A | 7/1998 | Felblinger et al. |
| 5,814,076 A | 9/1998 | Brownlee |
| 5,827,997 A | 10/1998 | Chung et al. |
| 5,842,966 A | 12/1998 | Markoll |
| 5,905,627 A | 5/1999 | Brendel et al. |
| 5,964,705 A | 10/1999 | Truwit et al. |
| 6,033,408 A | 3/2000 | Gage et al. |
| 6,101,417 A | 8/2000 | Vogel et al. |
| 6,198,972 B1 | 3/2001 | Hartlaub et al. |
| 6,209,764 B1 | 4/2001 | Hartlaub et al. |
| 6,258,071 B1 | 7/2001 | Brookes |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |
| 6,538,191 B1 | 3/2003 | MacDonald |
| 6,640,137 B2 | 10/2003 | MacDonald |
| 6,660,116 B2 | 12/2003 | Wolf et al. |
| 6,673,999 B1 | 1/2004 | Wang et al. |
| 6,675,033 B1 | 1/2004 | Lardo et al. |
| 6,695,761 B2 | 2/2004 | Oschman et al. |
| 6,708,051 B1 | 3/2004 | Durousseau |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,741,892 B1 | 5/2004 | Meadows et al. |
| 6,750,055 B1 | 6/2004 | Connelly et al. |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,768,053 B1 | 7/2004 | Wang et al. |
| 6,778,856 B2 | 8/2004 | Connelly et al. |
| 6,793,642 B2 | 9/2004 | Connelly et al. |
| 6,795,730 B2 | 9/2004 | Connelly et al. |
| 6,795,736 B2 | 9/2004 | Connelly et al. |
| 6,871,091 B2 | 3/2005 | Wilkinson et al. |
| 6,944,489 B2 | 9/2005 | Zeijlemaker et al. |
| 6,985,775 B2 | 1/2006 | Reinke et al. |
| 2002/0032468 A1 | 3/2002 | Hill et al. |
| 2002/0038135 A1 | 3/2002 | Connelly et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0183740 A1 | 12/2002 | Edwards et al. |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0109901 A1 | 6/2003 | Greatbatch |
| 2003/0120148 A1 | 6/2003 | Pacetti |
| 2003/0135114 A1 | 7/2003 | Pacetti et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144716 A1 | 7/2003 | Reinke et al. |
| 2003/0144717 A1 | 7/2003 | Hegele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 * | 7/2003 | Villaseca et al. ............ 607/122 |
| 2004/0068307 A1 * | 4/2004 | Goble ............... 607/101 |
| 2004/0098074 A1 * | 5/2004 | Erickson et al. ............ 607/117 |

FOREIGN PATENT DOCUMENTS

| | | |
|---|---|---|
| EP | 0 760 196 B1 | 3/1997 |
| EP | 1 273 922 A1 | 1/2003 |
| JP | 07/255863 | 10/1995 |
| WO | WO 97/41923 | 11/1997 |
| WO | WO 99/10035 | 3/1999 |
| WO | WO 99/19020 | 4/1999 |
| WO | WO 99/60370 | 11/1999 |
| WO | WO 00/27279 | 5/2000 |
| WO | WO 03/037429 A1 | 5/2003 |
| WO | WO 03/063948 A3 | 8/2003 |
| WO | WO 03/063952 A3 | 8/2003 |
| WO | WO 03/063953 A3 | 8/2003 |
| WO | WO 03/063954 A1 | 8/2003 |
| WO | WO 03/063955 A1 | 8/2003 |
| WO | WO 03/063956 A2 | 8/2003 |
| WO | WO 03/063957 A3 | 8/2003 |
| WO | WO 03/075797 A3 | 9/2003 |
| WO | WO 03/092326 A3 | 11/2003 |
| WO | WO 03/095022 A2 | 11/2003 |

| | | |
|---|---|---|
| WO | WO 04/052448 A1 | 6/2004 |
| WO | WO 04/073040 A3 | 8/2004 |

OTHER PUBLICATIONS

Finelli, D. et al.: "MR Imaging-Related Heating of Deep Brain Stimulation Electrodes: In Vitro Study"; AJNR AM J Neuroadiol 23:1, Nov./Dec. 2002.

Baker, K. et al.: "Evaluation of Specific Absorption Rate as a Dosimeter of MRI-Related Implant Heating"; Journal of Magnetic Resonance Imaging 20:315-320 (2004).

Rezai, A. et al.; "Neurostimulation System Used for Deep Brain Stimulation (DBS): MR Safety Issues and Implications of Failing to Follow Safety Recommendations" Investigati . . . .

Rezai, A. et al.; "Neurostimulation Systems for Deep Brain Stimulation In Vitro Evaluation of Magnetic Resonance Imaging-Related Heating at 1.5 Tesla"; Journal of Magnetic . . . .

Medtronic Activa Product Family and Procedure Solution Brochure.

Medtronic Neurostimulation Systems Brochure.

* cited by examiner

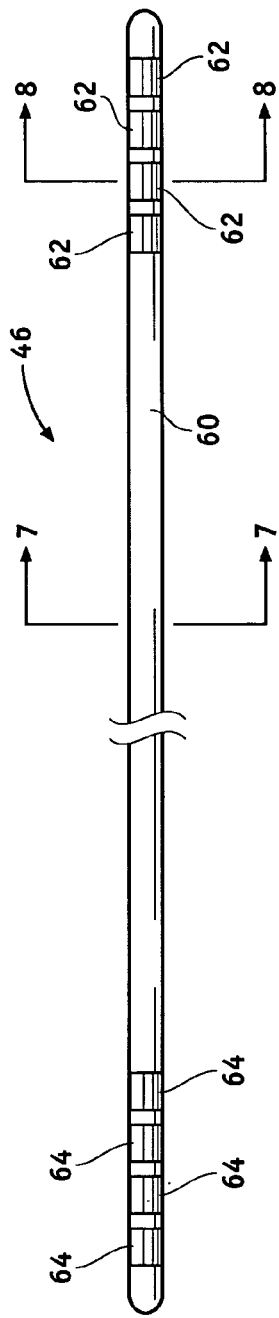
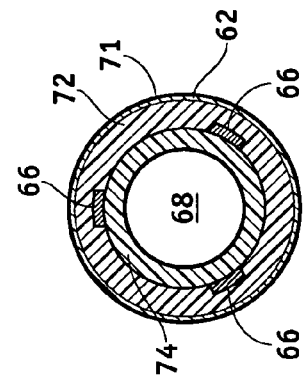
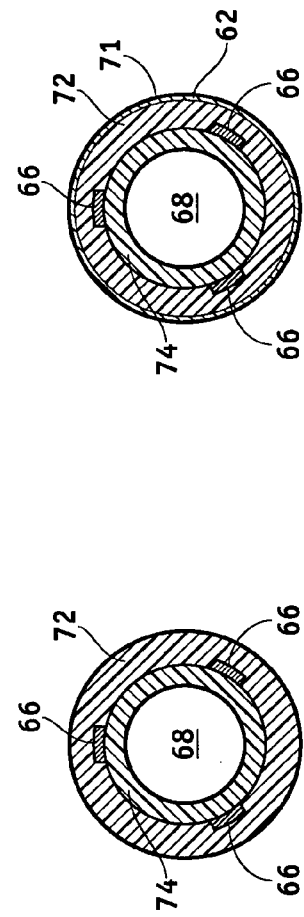
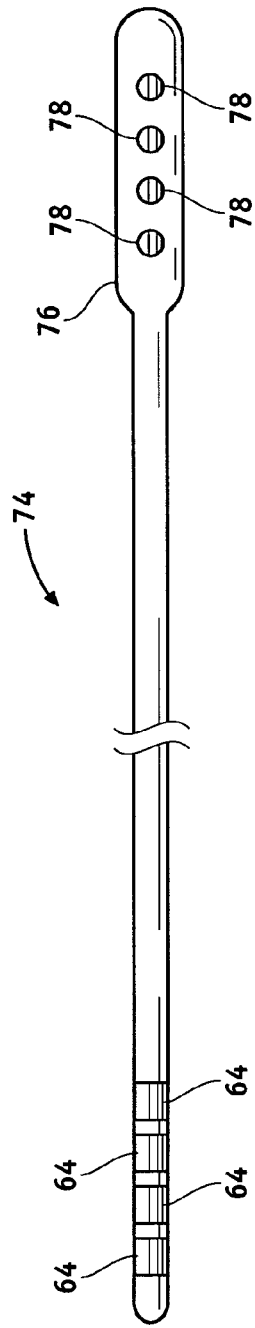
FIG. 6
FIG. 7
FIG. 8
FIG. 9

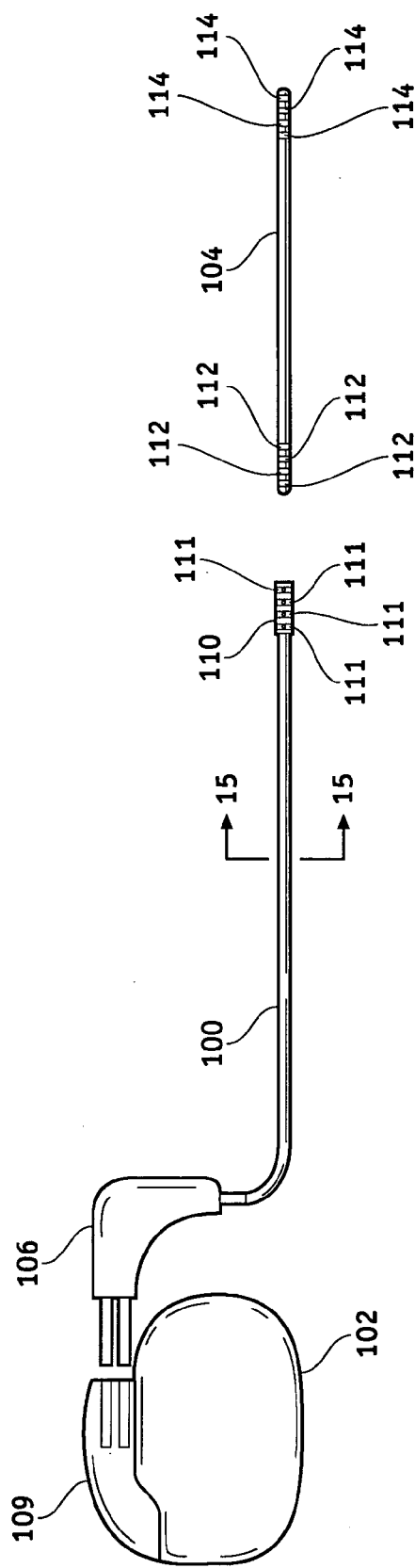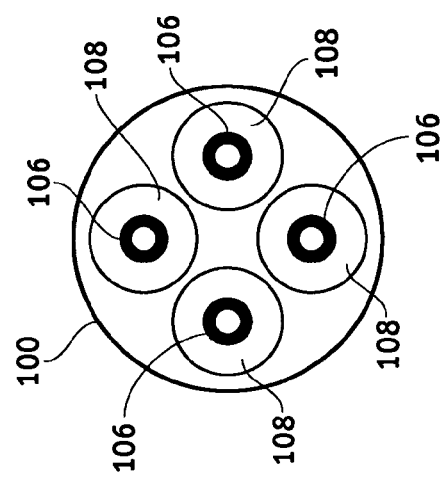
FIG. 14
FIG. 15

LEAD ELECTRODE FOR USE IN AN MRI-SAFE IMPLANTABLE MEDICAL DEVICE

CROSS-REFERENCES TO RELATED APPLICATIONS

This application claims the benefit of U.S. Provisional Application No. 60/557,991, filed Mar. 30, 2004.

FIELD OF THE INVENTION

The present invention generally relates to implantable medical devices, and more particularly to a lead electrode for use in conjunction with an implantable medical device such as a neurostimulation system which, when used in an MRI (Magnetic Resonance Imaging) environment, dissipates or directs energy at MRI frequencies to a patient's body in a safe manner.

BACKGROUND OF THE INVENTION

Implantable medical devices are commonly used today to treat patients suffering from various ailments. Such implantable devices may be utilized to treat conditions such as pain, incontinence, sleep disorders, and movement disorders such as Parkinson's disease and epilepsy. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer. Current systems generally include a non-rechargeable primary cell neurostimulator, a lead extension, and a stimulation lead, and the two main classes of systems may be referred to as: (1) Spinal Cord Stimulation (SCS) and (2) Deep Brain Stimulation (DBS).

An SCS stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinbelow) currently contains from one to eight electrodes. Each extension (likewise to be discussed in detail below) is plugged into or connected to the neurostimulator at a proximal end thereof and is coupled to and interfaces with the lead or leads at a distal end of the extension.

The implanted neurostimulation system is configured to send mild electrical pulses to the spinal cord. These electrical pulses are delivered through the lead or leads to regions near the spinal cord or a nerve selected for stimulation. Each lead includes a small insulated wire coupled to an electrode at the distal end thereof through which the electrical stimulation is delivered. Typically, the lead also comprises a corresponding number of internal wires to provide separate electrical connection to each electrode such that each electrode may be selectively used to provide stimulation. Connection of the lead to an extension may be accomplished by means of a connector block including, for example, a series or combination of set screws, ball seals, etc. The leads are inserted into metal set screw bocks, and the metal set screws are manipulated to press the contacts against the blocks to clamp them in place and provide electrical connection between the lead wires and the blocks. Such an arrangement is shown in U.S. Pat. No. 5,458,629 issued Oct. 17, 1995 and entitled "Implantable Lead Ring Electrode and Method of Making".

A DBS system comprises similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to eight electrodes and, as was the case previously, the proximal end of the lead may be connected to the distal end of the extension and may be held in place by set screws. The proximal portion of the extension plugs into the connector block of the neurostimulator.

Magnetic resonance imaging (MRI) is a relatively new and efficient technique that may be used in the diagnosis of many neurological disorders. It is an anatomical imaging tool which utilizes non-ionizing radiation (i.e. no x-rays or gamma rays) and provides a non-invasive method for the examination of internal structure and function. For example, MRI permits the study of the overall function of the heart in three dimensions significantly better than any other imaging method. Furthermore, imaging with tagging permits the non-invasive study of regional ventricular function.

MRI scanning is widely used in the diagnosis of injuries to the head. In fact, the MRI is now considered by many to be the preferred standard of care, and failure to prescribe MRI scanning can be considered questionable. Approximately sixteen million MRIs were performed in 1996, followed by approximately twenty million in the year 2000. It is projected that forty million MRIs will be performed in 2004.

In an MRI scanner, a magnet creates a strong magnetic field which aligns the protons of hydrogen atoms in the body and then exposes them to radio frequency (RF) energy from a transmitter portion of the scanner. This spins the various protons, and they produce a faint signal that is detected by a receiver portion of the scanner. A computer renders these signals into an image. During this process, three electromagnetic fields are produced; i.e. (1) a static magnetic field, (2) a gradient magnetic field, and (3) a radio frequency (RF) magnetic field. The main or static magnetic field may typically vary between 0.2 and 3.0 Tesla. A nominal value of 1.5 Tesla is approximately equal to 15,000 Gauss which is 30,000 times greater than the Earth's magnetic field of approximately 0.5 Gauss. The time varying or gradient magnetic field may have a maximum strength of approximately 40 milli-Tesla/meters at a frequency of 0–5 KHz. The RF may, for example, produce thousands of watts at frequencies of between 8–215 MHz. For example, up to 20,000 watts may be produced at 64 MHz and a static magnetic field of 1.5 Tesla; that is, 20 times more power than a typical toaster. Thus, questions have arisen regarding the potential risk associated with undesirable interaction between the MRI environment and the above-described neurostimulation systems; e.g. forces and torque on the implantable device within the MRI scanner caused by the static magnetic field, RF-induced heating, induced currents due to gradient magnetic fields, device damage, and image distortion. Of these interactions, the problems associated with induced RF currents in the leads are most deserving of attention since it has been found that the temperature in the leads can rise by as much as 25° Centigrade or higher in an MRI environment.

Accordingly, it would be desirable to provide an implantable medical device that may be safely operated in an MRI environment. It would be further desirable to provide an implantable medical device such as a SCS or DBS neurostimulation system that may be operated in an MRI environment without the generation of significant heat in the leads due to induced RF currents. It would be further desirable to provide a lead electrode that may be used in conjunction with known implantable medical devices that dissipated RF currents induced at MRI frequencies. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

According to an aspect of the invention, there is provided an electrode assembly for use in a pulse stimulation system configured to be implanted in a patient's body and of the type that includes a pulse generator and a stimulation lead having a proximal end electrically coupled to the pulse generator and having a distal region. The electrode assembly comprises an electrode body in the distal region of the stimulator lead and at least one electrode in the electrode body and electrically coupled to the stimulation leads for delivering therapy to the patient. A floating electrode is configured to contact the patient's body tissue and has a surface area substantially larger than the surface area of the therapy electrode. A filter such as a band-pass or high-pass filter is coupled between the therapy electrode and the floating electrode for diverting RF energy toward the floating electrode and away from the therapy electrode.

According to a further aspect of the invention, there is provided an electrode assembly for use in a pulse stimulation system configured to be implanted in a patient's body and of the type that includes a pulse generator and a stimulation lead having a proximal end electrically coupled to the pulse generator and has a distal region. The electrode assembly comprises a paddle-shaped electrode body having first and second substantially opposite sides, and the body is coupled to the distal region of the stimulation lead. At least one electrode within the body is electrically coupled to the stimulation lead and at least one electrode has a first side for delivering therapy to the patient and has a second side. Alternating layers of conducting and non-conducting material are stacked on the second side to capacitively couple the electrode to the patient's body tissue for delivering RF energy to the patient's body tissue.

According to still another further aspect of the invention, there is provided an electrode assembly for use in a pulse stimulation system configured to be implanted in a patient's body and of the type that includes a pulse generator and a stimulation lead having a proximal end electrically coupled to the pulse generator and has a distal region. The electrode assembly comprises a paddle-shaped electrode body and has first and second substantially opposite sides, and the body is coupled to the distal region of the stimulation lead. At least one electrode is within said body and is electrically coupled to the stimulation lead, and the electrode has a first side for delivering therapy to the patient. The electrode has a second side and a layer of dielectric material on the second side. It is configured to capacitively couple the electrode to the patient's body for delivering RF energy to the patient's body.

BRIEF DESCRIPTION OF THE DRAWINGS

The present invention will hereinafter be described in conjunction with the following drawing figures, wherein like numerals denote like elements, and:

FIG. 6 is a top view of the lead shown in FIG. 2;

FIGS. 7 and 8 are cross-sectional views taken along lines 7—7 and 8—8, respectively, in FIG. 6;

FIG. 9 is a top view of an alternate lead configuration;

FIG. 14 is an exploded view of a neurostimulation system;

FIG. 15 is a cross-sectional view of the extension shown in FIG. 14 taken along line 15—15;

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
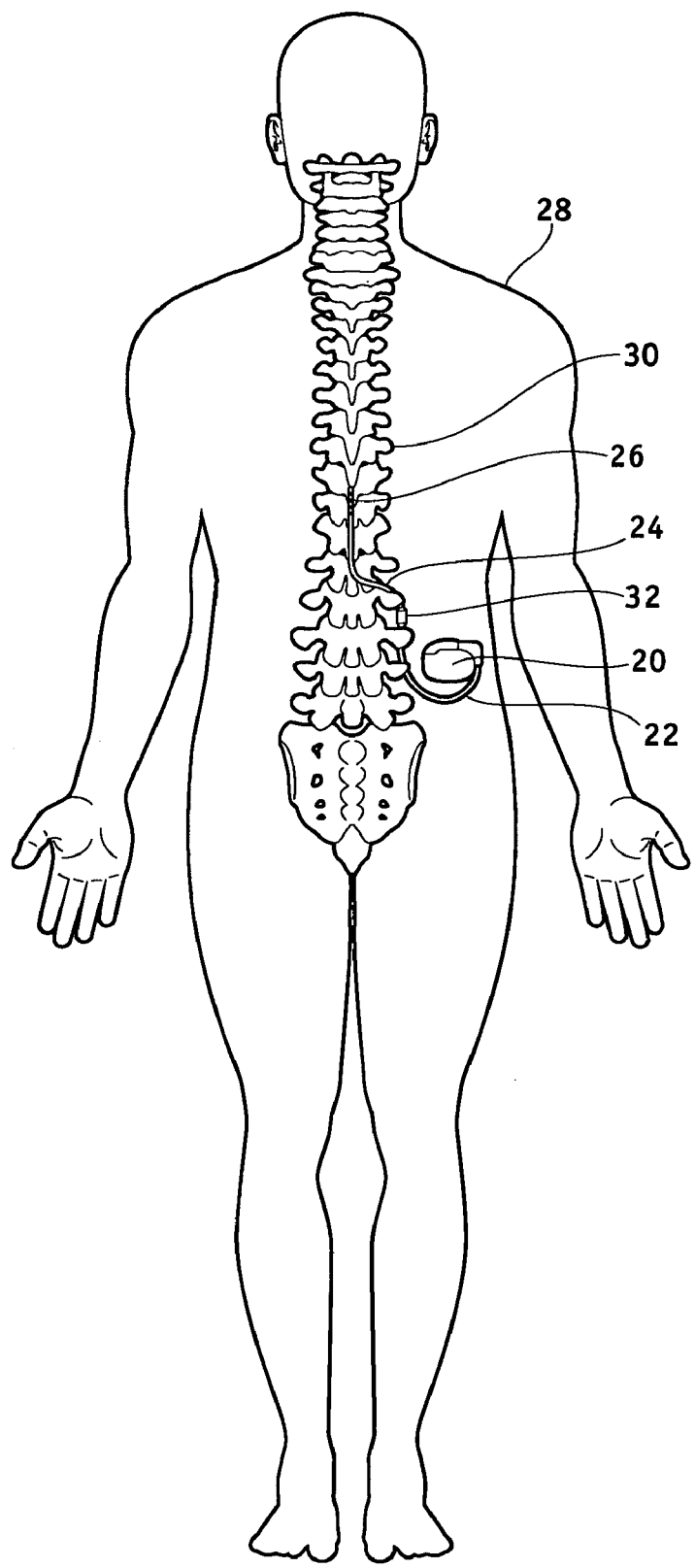
FIG. 1 illustrates a typical spinal cord stimulation system implanted in a patient.

FIG. 1 illustrates a typical SCS system implanted in a patient. As can be seen, the system comprises a pulse generator such as an SCS neurostimulator 20, a lead extension 22 having a proximal end coupled to neurostimulator 20 as will be more fully described below, and a lead 24 having proximal end coupled to the distal end of extension 22 and having a distal end coupled to one or more electrodes 26. Neurostimulator 20 is typically placed in the abdomen of a patient 28, and lead 24 is placed somewhere along spinal cord 30. As stated previously, neurostimulator 20 may have one or two leads each having four to eight electrodes. Such a system may also include a physician programmer and a patient programmer (not shown). Neurostimulator 20 may be considered to be an implantable pulse generator of the type available from Medtronic, Inc. and capable of generating multiple pulses occurring either simultaneously or one pulse shifting in time with respect to the other, and having independently varying amplitudes and pulse widths. Neurostimulator 20 contains a power source and the electronics for sending precise, electrical pulses to the spinal cord to provide the desired treatment therapy. While neurostimulator 20 typically provides electrical stimulation by way of pulses, other forms of stimulation may be used as continuous electrical stimulation.

Lead 24 is a small medical wire having special insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). Lead 24 may contain a paddle at its distant end for housing electrodes 26; e.g. a Medtronic paddle having model number 3587A. Alternatively, electrodes 26 may comprise one or more ring contacts at the distal end of lead 24 as will be more fully described below.

While lead 24 is shown as being implanted in position to stimulate a specific site in spinal cord 30, it could also be positioned along the peripheral nerve or adjacent neural tissue ganglia or may be positioned to stimulate muscle tissue. Furthermore, electrodes 26 may be epidural, intrathecal or placed into spinal cord 30 itself. Effective spinal cord stimulation may be achieved by any of these lead placements. While the lead connector at proximal end of lead 24 may be coupled directly to neurostimulator 20, the lead connector is typically coupled to lead extension 22 as is shown in FIG. 1. An example of a lead extension is Model 7495 available from Medtronic, Inc.

A physician's programmer (not shown) utilizes telemetry to communicate with the implanted neurostimulator 20 to enable the physician to program and manage a patient's therapy and troubleshoot the system. A typical physician's programmer is available from Medtronic, Inc. and bears Model No. 7432. Similarly, a patient's programmer (also not shown) also uses telemetry to communicate with neurostimulator 20 so as to enable the patient to manage some aspects of their own therapy as defined by the physician. An example of a patient programmer is Model 7434® 3 EZ Patient Programmer available from Medtronic, Inc.

Implantation of a neurostimulator typically begins with the implantation of at least one stimulation lead usually while the patient is under a local anesthetic. While there are many spinal cord lead designs utilized with a number of different implantation techniques, the largest distinction between leads revolves around how they are implanted. For example, surgical leads have been shown to be highly effective, but require a laminectomy for implantation. Percutaneous leads can be introduced through a needle, a much easier procedure. To simplify the following explanation, discussion will focus on percutaneous lead designs, although it will be understood by those skilled in the art that the inventive aspects are equally applicable to surgical leads.

After the lead is implanted and positioned, the lead's distal end is typically anchored to minimize movement of the lead after implantation. The lead's proximal end is typically configured to connect to a lead extension 22. The proximal end of the lead extension is then connected to the neurostimulator 20.

Figure 2:
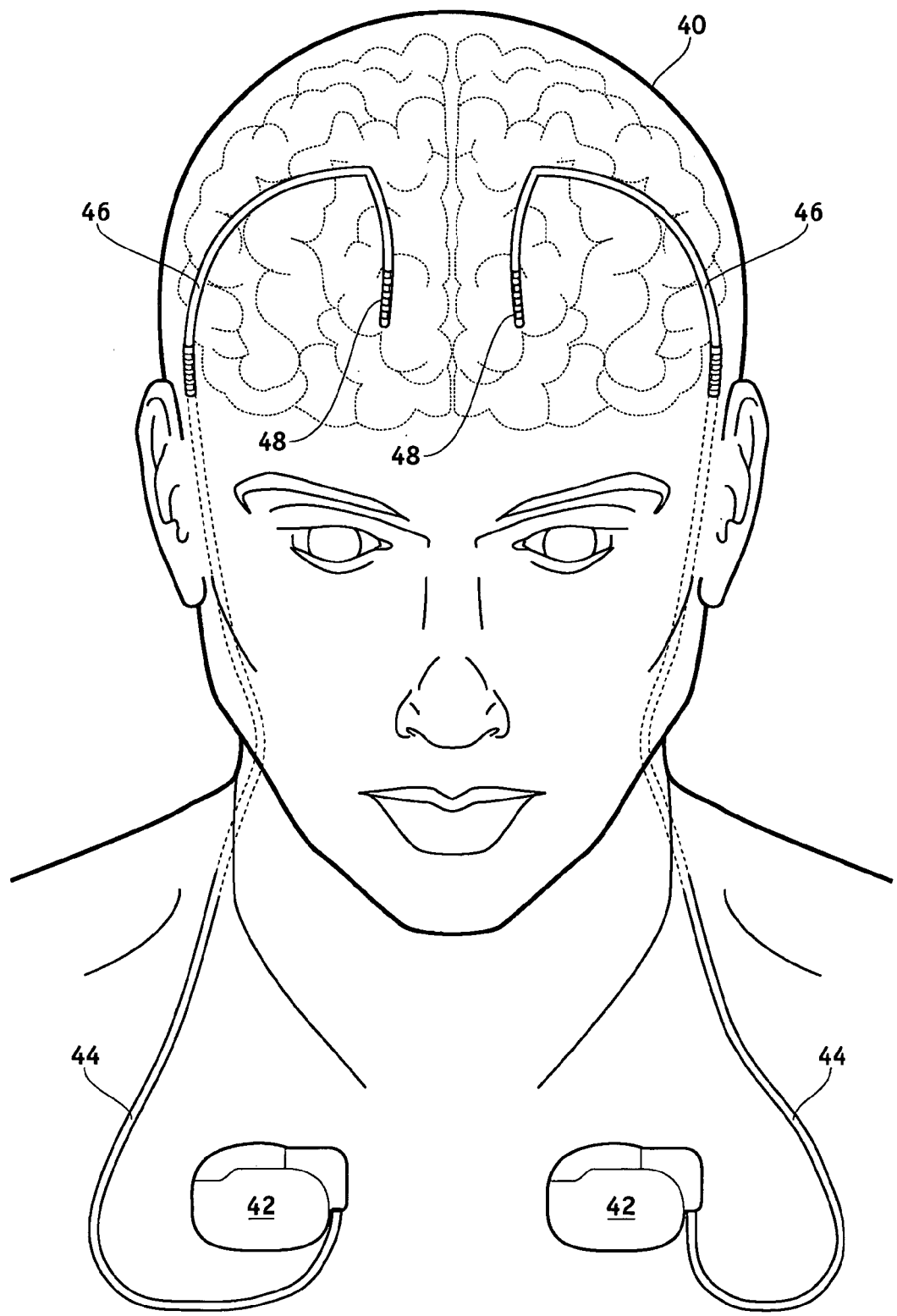
FIG. 2 illustrates a typical deep brain stimulation system implanted in a patient.

FIG. 2 illustrates a DBS system implanted in a patient 40 and comprises substantially the same components as does an SCS; that is, at least one neurostimulator, at least one extension, and at least one stimulation lead containing one or more electrodes. As can be seen, each neurostimulator 42 is implanted in the pectoral region of the patient. Extensions 44 are deployed up through the patient's neck, and leads 46 are implanted in the patient's brain is as shown at 48. As can be seen, each of the leads 46 is connected to its respective extension 44 just above the ear on both sides of patient 40.

Figure 5:
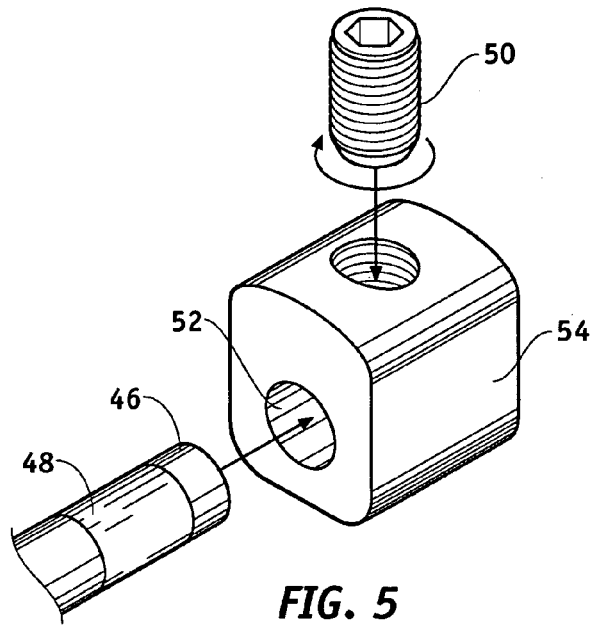
FIG. 5 is an isometric view of an example of a connector screw block suitable for connecting the lead of FIG. 3 to the extension shown in FIG. 4.
Figure 3:
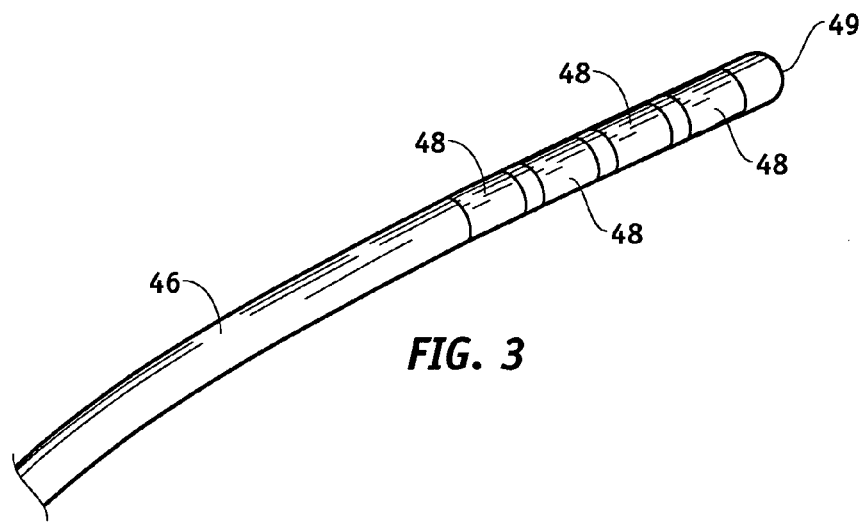
FIG. 3 is an isometric view of the distal end of the lead shown in FIG. 2.
Figure 4:
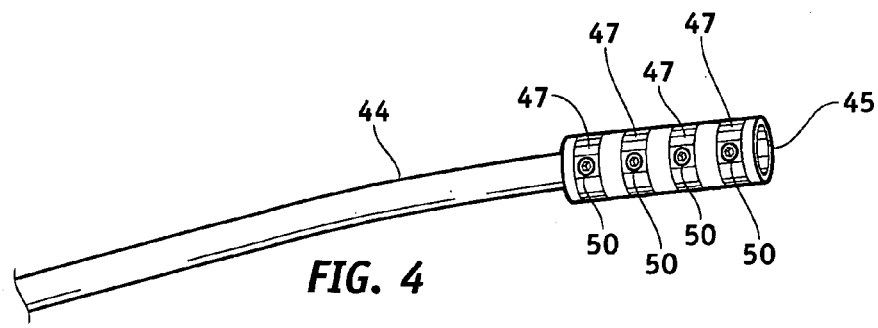
FIG. 4 is an isometric view of the distal end of the extension shown in FIG. 2.

FIG. 3 is an isometric view of the distal end of lead 46. In this case, four ring electrodes 48 are positioned on the distal end of lead 46 and coupled to internal conductors of filers (not shown) contained within lead 46. Again, while four ring electrodes are shown in FIG. 3, it is to be understood that the number of electrodes can vary to suit a particular application. FIG. 4 is an isometric view of the distal end of extension 44, which includes a connector portion 45 having four internal contacts 47. The proximal end of the DBS lead is shown in FIG. 3, plugs into the distal connector 45 of extension 44, and is held in place by means of, for example, a plurality (e.g. 4) of set screws 50. For example, referring to FIG. 5, lead 46 terminates in a series of proximal electrical ring contacts 48 (only one of which is shown in FIG. 5). Lead 46 may be inserted through an axially aligned series of openings 52 (again only one shown) in screw block 54. With a lead 46 so inserted, a series of set screws (only one shown) are screwed into block 54 to drive contacts 48 against blocks 54 and secure and electrically couple the lead 46. It should be appreciated, however, that other suitable methods for securing lead 46 to extension 44 may be employed. The proximal portion of extension 44 is secured to neurostimulator 42 as is shown in FIGS. 1 and 2.

FIG. 6 is a top view of lead 46 shown in FIG. 2. FIGS. 7 and 8 are cross-sectional views taken along lines 7—7 and 8—8, respectively, in FIG. 6. Distal end 60 of lead 46 includes at least one electrode 62 (four are shown). As stated previously, up to eight electrodes may be utilized. Each of electrodes 62 is preferably constructed as is shown in FIG. 8. That is, electrode 62 may comprise a conductive ring 71 on the outer surface of the elongate tubing making up distal shaft 60. Each electrode 62 is electrically coupled to a longitudinal wire 66 (shown in FIGS. 7 and 8) each of which extends to a contact 64 at the proximal end of lead 46. Longitudinal wires 66 may be of a variety of configurations; e.g. discreet wires, printed circuit conductors, etc. From the arrangement shown in FIG. 6, it should be clear that four conductors or filers run through the body of lead 46 to electrically connect the proximal electrodes 64 to the distal electrodes 62. As will be further discussed below, the longitudinal conductors 66 may be spirally configured along the axis of lead 46 until they reach the connector contacts.

The shaft of lead 46 preferably has a lumen 68 extending therethrough for receiving a stylet that adds a measure of rigidity during installation of the lead. The shaft preferably comprises a comparatively stiffer inner tubing member 70 (e.g. a polyamine, polyamide, high density polyethylene, polypropylene, polycarbonate or the like). Polyamide polymers are preferred. The shaft preferably includes a comparatively softer outer tubing member 72; e.g. silicon or other suitable elastomeric polymer. Conductive rings 71 are preferably of a biocompatible metal such as one selected from the noble group of metals, preferably palladium, platinum or gold and their alloys.

FIG. 9 illustrates an alternative lead 74 wherein distal end 76 is broader (e.g. paddle-shaped) to support a plurality of distal electrodes 78. A lead of this type is shown in FIG. 1. As was the case with the lead shown in FIGS. 6, 7, and 8, distal electrodes 78 are coupled to contacts 64 each respectively by means of an internal conductor or filer. A more detailed description of the leads shown in FIGS. 6 and 9 may be found in U.S. Pat. No. 6,529,774 issued Mar. 4, 2003 and entitled "Extradural Leads, Neurostimulator Assemblies, and Processes of Using Them for Somatosensory and Brain Stimulation".

Figure 11:
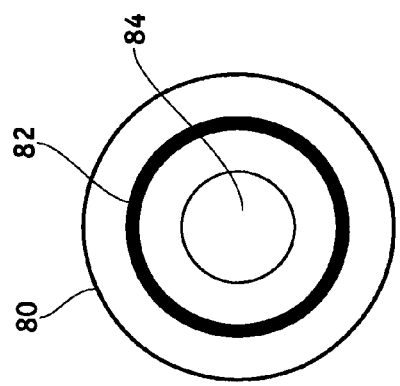
FIGS. 10 and 11 are longitudinal and radial cross-sectional views of a helically wound lead of the type shown in FIG. 6.
Figure 10:
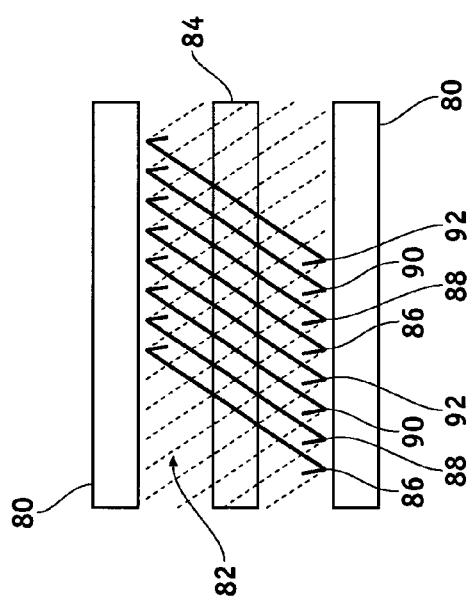

Leads of the type described above may be of the wound helix filer type or of the cabled filer type. FIGS. 10 and 11 are longitudinal and radial cross-sectional views, respectively, of a helically wound lead of the type shown in FIG. 6. The lead comprises an outer lead body 80; a plurality of helically wound, co-radial lead filers 82; and a stylet lumen 84. As stated previously, a stylet is a stiff, formable insert placed in the lead during implant so as to enable the physician to steer the lead to an appropriate location. FIG. 10 illustrates four separate, co-radially wound filers 86, 88, 90, and 92 which are electrically insulated from each other and electrically couple a single electrode 62 (FIG. 6) to a single contact 64 (FIG. 6).

Figure 13:
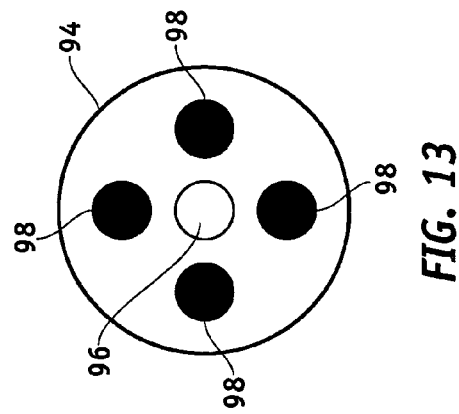
FIGS. 12 and 13 are longitudinal and radial cross-sectional views, respectively, of a cabled lead.
Figure 12:
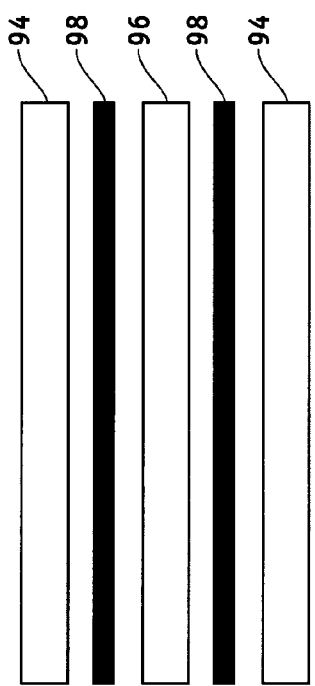

As can be seen, lead filers 82 have a specific pitch and form a helix of a specific diameter. The helix diameter is relevant in determining the inductance of the lead. These filers themselves also have a specific diameter and are made of a specific material. The filer diameter, material, pitch and helix diameter are relevant in determining the impedance of the lead. In the case of a helically wound lead, the inductance contributes to a frequency dependent impedance. FIGS. 12 and 13 are longitudinal and radially cross-sectional views, respectively, of a cabled lead. The lead comprises outer lead body 94, stylet lumen 96, and a plurality (e.g. four to eight) of straight lead filers 98.

FIG. 14 is an exploded view of a neurostimulation system that includes an extension 100 configured to be coupled between a neurostimulator 102 and lead 104. The proximal portion of extension 100 comprises a connector 106 configured to be received or plugged into connector block 109 of neurostimulator 102. The distal end of extension 100 likewise comprises a connector 110 including internal contacts 111 and is configured to receive the proximal end of lead 104 having contacts 112 thereon. The distal end of lead 104 includes distal electrodes 114.

FIG. 15 is a cross-sectional view of extension 100. Lead extension 100 has a typical diameter of 0.1 inch, which is significantly larger than that of lead 104 so as to make extension 100 more durable than lead 104. Extension 100 differs from lead 104 also in that each filer 106 in lead body is helically wound or coiled in its own lumen 108 and not co-radially wound with the rest of the filers as was the case in lead 104.

The diameter of typical percutaneous leads is approximately 0.05 inch. This diameter is based upon the diameter of the needle utilized in the surgical procedure to deploy the lead and upon other clinical anatomical requirements. The length of such percutaneous SCS leads is based upon other clinical anatomical requirements. The length of such percutaneous SCS leads is typically 28 centimeters; however, other lengths are utilized to meet particular needs of specific patients and to accommodate special implant locations.

Lead length is an important factor in determining the suitability of using the lead in an MRI environment. For example, the greater length of the lead, the larger the effective loop area that is impacted by the electromagnetic field (e.g. the longer the lead, the larger the antenna). Furthermore, depending on the lead length, there can be standing wave effects that create areas of high current along the lead body. This can be problematic if the areas of high current are near the distal electrodes.

Compared to the helically wound lead, the cable lead has smaller DC resistance because the length of the straight filer is less than that of a coiled filer and the impedance at frequency is reduced because the inductance has been significantly reduced. It has been determined that the newer cabled filer designs tend to be more problematic in an MRI environment than do the wound helix filer designs. It should be noted that straight filers for cable leads sometimes comprise braided stranded wire that includes a number of smaller strands woven to make up each filer. This being the case, the number of strands could be varied to alter the impedance.

As stated previously, the electromagnetic fields within an MRI environment produce RF currents in the leads that can result in the production of heat and accompanying undesirable temperature increases at the lead electrodes. A lead arrangement for minimizing this problem is shown in FIGS. 16 and 17 which are top and bottom views respectively, of the inventive electrode assembly.

Figure 16:
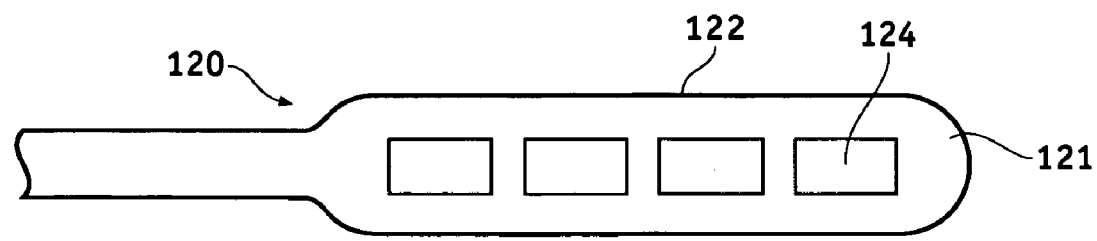
FIG. 16 is a top view of an implantable paddle lead in accordance with a first embodiment of the present invention.
Figure 17:
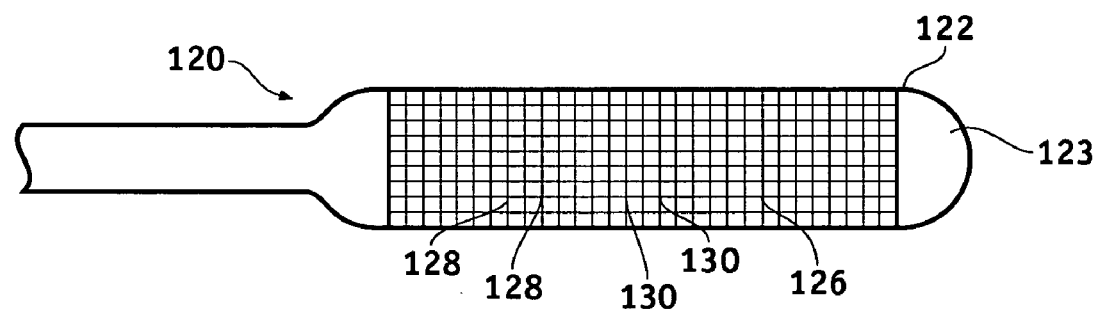
FIG. 17 is a bottom view of the lead shown in FIG. 16.

Referring to FIGS. 16 and 17, the distal region 120 of an implantable lead includes a paddle-shaped lead body 122 (typically a flexible polymer or other similar material) having a first surface 121 and a second opposite surface 123. At least one therapy electrode 124 is positioned on surface 121. While four such electrodes are shown in FIG. 16, it is to be understood that the number of electrodes may vary with different therapy regimens. As previously described, each electrode 124 is internally electrically coupled to a conductive filer (e.g. 98 in FIGS. 12 and 13) which is in turn electrically coupled to a pulse generator (e.g. neurostimulator 102 in FIG. 14) for the purpose of conducting stimulation pulses to a patient.

The paddle electrode assembly shown in FIGS. 16 and 17 is configured to safely dissipate the energy created during an MRI scan by directing the induced currents to a floating electrode having a large surface. For this purpose, a conductive mesh plate 126 comprises a plurality of longitudinal conductors 128 that are intersected by a plurality of transverse conductors 130. Conductive mesh 126 may be imbedded in the underside of paddle 122 as indicated in FIG. 17 and as will be more fully described below. By directing the currents induced in the filers during an MRI scan from electrodes 124 to conductive mesh 126, the induced current is spread over a large surface area (e.g. an order of magnitude greater than the surface area of electrodes 124) and thus, body tissue in contact with mesh 126 will not be damaged.

Figure 18:
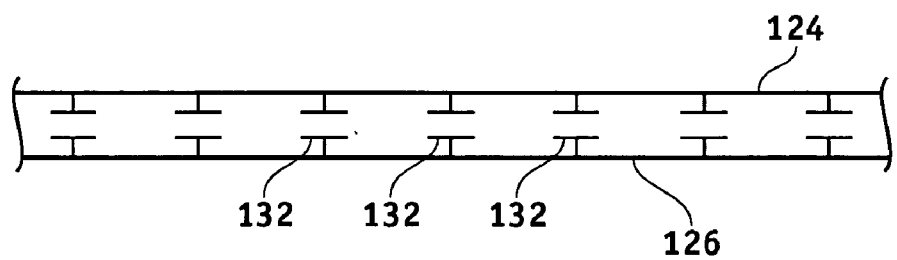
FIG. 18 is a side view illustrating one technique for imbedding a conductive mesh plate into the paddle lead shown in FIG. 16.

Since the issue of induced RF currents becomes problematic in the high frequency MRI environment, high-pass or band-pass filters may be coupled between electrodes 124 and mesh 126 to ensure that current does not flow to mesh plate 126 at pulse stimulation frequencies. Such high-pass filters may be simple capacitors 132 as shown in FIG. 18.

Figure 19:
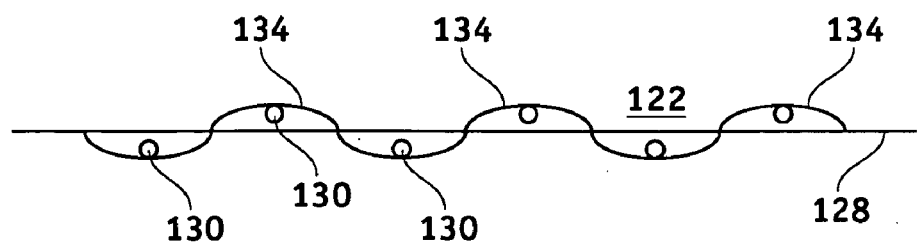
FIG. 19 is a side view illustrating a second technique for imbedding a conductive mesh plate into the paddle lead shown in FIG. 16.

Conductive mesh plate 126 may be configured to cover the entire posterior side of paddle electrode 122 in order to achieve the desired surface area. For example, while electrodes 124 may have a surface area of approximately 10 square millimeters, conductive mesh plate 126 may have a surface area of approximately 120 square millimeters. This configuration of mesh plate 126 provides for easy retention within the lead body 122 while still providing sufficient surface area in contact with the patient's tissue. If desired, mesh plate 126 may have a wavy configuration such as is shown in FIG. 19 to enable a portion of the mesh plate indicated at 134 to be captured in body 122 while the remainder of mesh plate 126 is exposed for contact with a patient's tissue.

Figure 20:
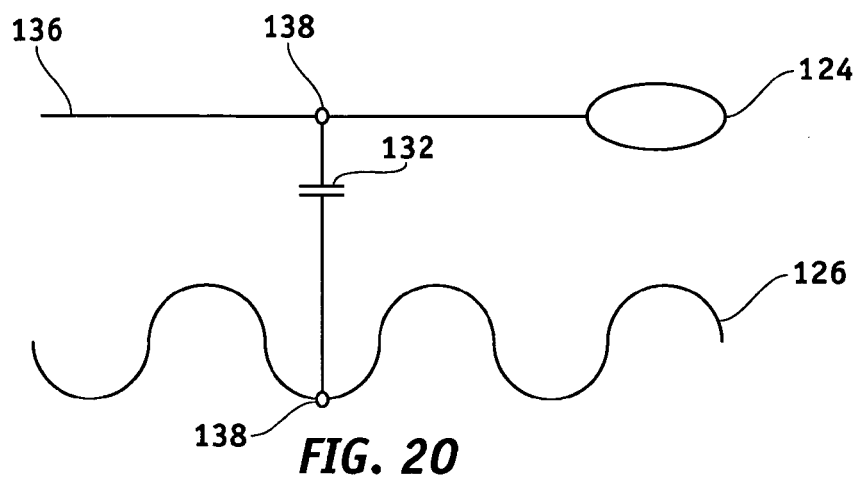
FIG. 20 is a schematic diagram illustrating a second embodiment of the inventive paddle lead.

FIG. 20 illustrates an exemplary embodiment of the present invention wherein the high-pass filter represented by capacitor 132 is coupled between mesh plate 126 and conductive filer 136 at a location proximal of electrode 124. In this way, induced RF energy will be diverted through capacitor 132 at high frequencies (MRI frequencies) to mesh plate 126 prior to reaching electrode 124. Capacitor 132 may be of the ceramic variety and therefore capable of withstanding the environment within a patient's body. Furthermore, if capacitor 132 is provided with leads, the leads could be crimped, cross-welded, or bonded using a conductive adhesive to filer 136 and mesh plate 126 as is shown at 138.

Since it is desirable that current flow to mesh 126 at MRI frequencies but not at stimulation frequencies, the high-pass filter must have high impedance at low frequency and low impedance at high frequency. As already stated, this may be accomplished, in its simplest form, by a single capacitor. It is know that the impedance of a capacitor is:

$$Z = 1/j\omega C \qquad \text{Equation (1)}$$

The maximum stimulation frequency is in the order of 1000 Hz, which is approximately four orders of magnitude lower than the lowest MRI frequency of approximately 43 MHz at 1.0 Tesla. Thus, it can be determined that capacitors in the range of 200 pF to 47,000 pF, preferably a 1000 pF, may be utilized to create a high-pass filter that acts with a high impedance at DC and stimulation frequencies and low impedance at MRI frequencies.

Figure 21:
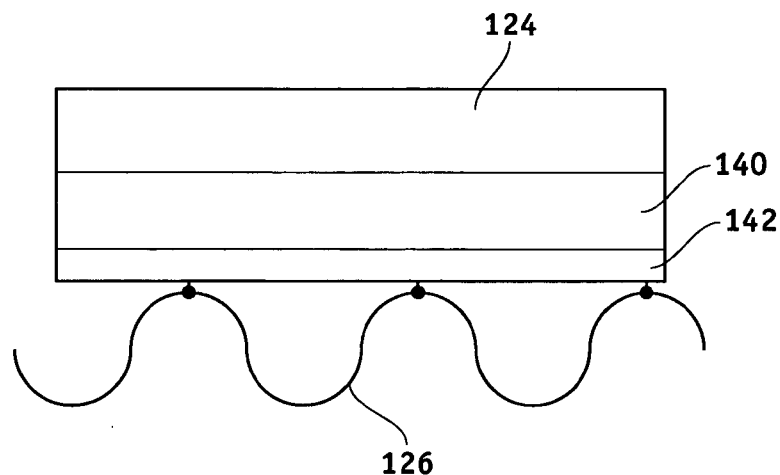
FIG. 21 is a schematic diagram of a third embodiment of the inventive paddle lead.

FIG. 21 illustrates another embodiment of the inventive lead electrode assembly. In this case, a dielectric material 140 (e.g. tantalum oxide) is placed between stimulation electrode 124 and mesh plate 126. An additional capacitor plate 142 may be provided between dielectric layer 140 and mesh plate 126 if more capacitance is needed or to provide a good connection mechanism to floating plate 126.

Figure 22:
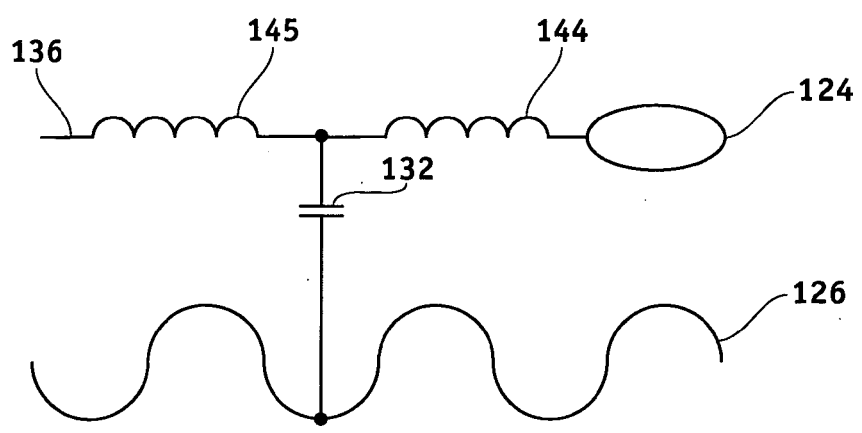
FIG. 22 illustrates the circuit of FIG. 20 having a mismatch component incorporated therein.

FIG. 22 is a schematic diagram of yet another embodiment of the inventive lead electrode assembly. As can be seen, the arrangement shown in FIG. 22 is substantially the same as that shown in FIG. 20 except that an inductor 144 has been inserted just proximal of electrode 124. While the impedance of capacitor 132 is low at MRI frequencies, in contrast the impedance of inductor 144 is high at MRI frequencies. Thus, induced currents flowing in filer 136 toward electrode 124 are further encouraged toward floating electrode 126 thus restricting the amount of current reaching stimulation electrode 124. If desired, an additional inductor 145 may be utilized as a replacement for or in addition to inductor 144. Inductor 145 is positioned between filer 136 and capacitor 132 and reflects at least a portion of the induced RF energy in a proximal direction along filer 136 at high frequency.

Figure 23:
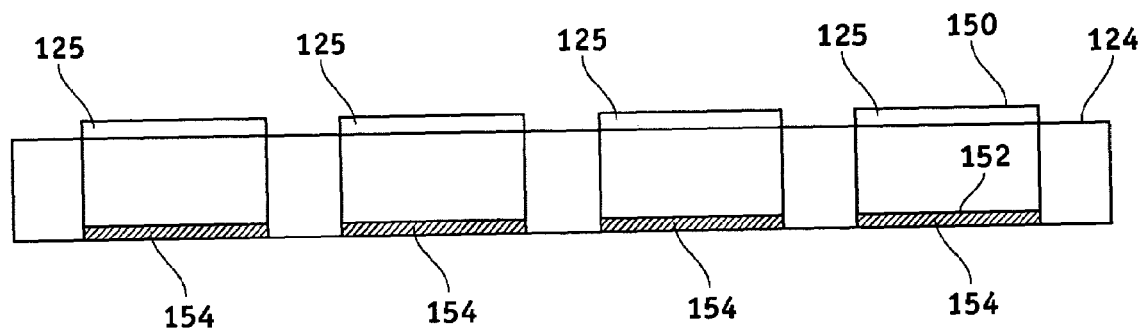
FIG. 23 illustrates yet a further embodiment of the present invention.

FIG. 23 illustrates yet another embodiment of the present invention. In this case, the stimulation electrodes 125 themselves also act as a floating electrode to provide capacitive coupling to the patient's body tissue or fluid. As can be seen, each stimulation electrode 124 comprises a stimulation surface 150 for transmitting a desired stimulation therapy to the patient and an opposite surface 152 that is covered to coated with a thin, dielectric or insulative layer 154 (e.g. a non-conductive polymer such as silicone, tantalum oxide, etc.), thus capacitively coupling electrode 125 to the patient's body tissue or fluid. Thus, in effect creates a contact with the patient's body tissue or fluid that has a greater effective surface area at high frequencies such as those encountered during an MRI scan. The amount of capacitance may be varied by selecting the thickness and/or material characteristics of layer 154 in accordance with known techniques.

Figure 24:
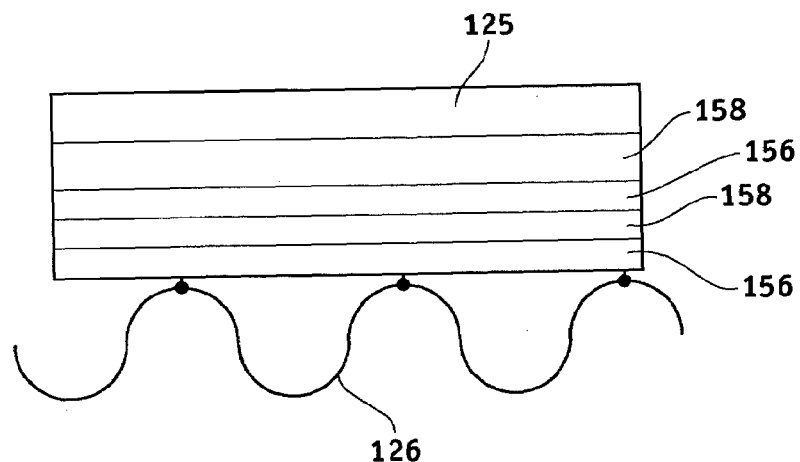
FIG. 24 illustrates a still further embodiment of the present invention.

In yet another embodiment of the invention shown in FIG. 24 alternating layers of conducting layers 156 (e.g. platinum, stainless steel, MP35n, etc.) and dielectric layers 158 (e.g. silicone) are utilized to capacitively couple electrode 124 to floating electrode (mesh 126) as previously described. Of course, mesh 126 is optional if the last layer 160 is conductive and is configured to be placed in contact with the patient's body tissue or fluid.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. An electrode assembly for use in a pulse stimulation system configured to be implanted in a patient's body and of the type that includes a pulse generator and a stimulation lead having a proximal end electrically coupled to the pulse generator and having a distal region, the electrode assembly comprising:
    a paddle-shaped electrode body having first and second substantially opposite sides, the body coupled to the distal region of the stimulation lead;
    at least one electrode on said first side and electrically coupled to the stimulation lead for delivering therapy to the patient;
    a floating electrode on said second side and configured to contact patient body tissue; and
    a filter coupled between said at least one electrode and said floating electrode for diverting RF energy toward said floating electrode and away from said at least one electrode.

2. An electrode assembly according to claim 1 wherein said RF energy is induced during an MRI scan.

3. An electrode assembly according to claim 1 wherein the RF energy is substantially diverted at frequencies between approximately 43 MHz to 215 MHz.

4. An electrode assembly according to claim 3 wherein said filter is a high-pass filter.

5. An electrode assembly according to claim 4 wherein said filter is a band-pass filter.

6. An electrode assembly according to claim 3 wherein the surface area of said floating electrode is at least an order of magnitude greater than that of said at least one electrode.

7. An electrode assembly according to claim 6 wherein the surface area of said floating electrode is at least approximately 120 square millimeters.

8. An electrode assembly according to claim 1 wherein the stimulation lead includes at least one conductive filer and said filter comprises at least one capacitor coupled between said at least one filer and said floating electrode.

9. An electrode assembly according to claim 8 wherein said capacitor has a capacitance in the range of 200 pF to 47,000 pF.

10. An electrode assembly according to claim 9 wherein said capacitor has a capacitance of approximately 1000 pF.

11. An electrode assembly according to claim 10 wherein said floating electrode comprises a conductive mesh.

12. An electrode assembly according to claim 11 wherein said conductive mesh is configured to have at least a portion thereof imbedded in said electrode body.

13. An electrode assembly according to claim 12 wherein said electrode body is a flexible polymer.

14. An electrode assembly according to claim 11 wherein said capacitor is coupled between said conductive mesh and said conductive filer proximal of said at least one electrode.

15. An electrode assembly according to claim 14 wherein said capacitor is coupled to said conductive mesh and to said conductive filer by crimping.

16. An electrode assembly according to claim 14 wherein said capacitor is coupled to said conductive mesh and to said conductive filer by welding.

17. An electrode assembly according to claim 16 wherein said capacitor is coupled to said conductive mesh by means of a conductive adhesive.

18. An electrode assembly according to claim 11 further comprising a dielectric material disposed between said at least one electrode and said conductive mesh.

19. An electrode assembly according to claim 18 wherein said dielectric material is tantalum oxide.

20. An electrode assembly according to claim 18 further comprising a capacitor plate coupled between said dielectric material and said conductive mesh.

21. An electrode assembly according to claim 14 further comprising an impedance mismatch component in the conduction path of said stimulation lead.

22. An electrode assembly according to claim 14 wherein said impedance mismatch component is coupled between said at least one electrode and said capacitor.

23. An electrode assembly according to claim 22 wherein said impedance mismatch component is an inductor.

24. A pulse stimulation system configured for implantation into a patient's body, the system comprising:
  a pulse generator;
  a conductive stimulation lead having a proximal end electrically coupled to said pulse generator and having a distal end; and
  an electrode assembly coupled to said distal end and comprising:
    a paddle-shaped electrode body having first and second substantially opposite sides, the body coupled to said distal end of said stimulation lead;
    at least one electrode on said first side and electrically coupled to said stimulation lead for delivering therapy to the patient;
    a floating electrode on said second side and configured to contact patient body tissue; and
    a filter coupled between said at least one electrode and said floating electrode for diverting RF energy toward said floating electrode and away from said at least one electrode.

25. An electrode assembly according to claim 24 wherein said RF energy is induced during an MRI scan.

26. An electrode assembly according to claim 24 wherein the RF energy is substantially diverted at frequencies between approximately 43 MHz to 215 MHz.

27. An electrode assembly according to claim 26 wherein said filter is a high-pass filter.

28. An electrode assembly according to claim 27 wherein said filter is a band-pass filter.

29. An electrode assembly according to claim 27 wherein the surface area of said floating electrode is at least an order of magnitude greater than that of said at least one electrode.

30. An electrode assembly according to claim 27 wherein said stimulation lead includes at least one conductive filer and said high-pass filter comprises at least one capacitor coupled between said at least one filer and said floating electrode.

31. An electrode assembly according to claim 30 wherein said capacitor has a capacitance in the range of 200 pF to 47,000 pF.

32. An electrode assembly according to claim 31 wherein said floating electrode comprises a conductive mesh.

33. An electrode assembly according to claim 32 wherein said conductive mesh is configured to have at least a portion thereof imbedded in said electrode body.

34. An electrode assembly according to claim 32 wherein said capacitor is coupled between said conductive mesh and said conductive filer proximal of said at least one electrode.

35. An electrode assembly according to claim 32 further comprising a dielectric material disposed between said at least one electrode and said conductive mesh.

36. An electrode assembly according to claim 35 wherein a capacitor plate is coupled between said dielectric material and said conductive mesh.

37. An electrode assembly according to claim 34 further comprising an impedance mismatch component coupled between said at least one electrode and said capacitor.

38. An electrode assembly according to claim 37 wherein said impedance mismatch component is an inductor.

39. An electrode assembly for use in a pulse stimulation system configured to be implanted in a patient's body and of the type that includes a pulse generator and a stimulation lead having a proximal end electrically coupled to the pulse generator and having a distal end, the electrode assembly comprising:
  a paddle-shaped electrode body coupled to the distal end of the stimulator lead, said electrode body having first and second sides;
  at least one conductive filer within the stimulation lead and electrically coupled to the pulse generator;
  at least one electrode positioned on said first side and coupled to said filer and configured to deliver therapy to the patient;
  a conductive mesh positioned on said second side and configured to contact the patient's body tissue; and
  a high-pass filter coupled between said at least one electrode and said conductive mesh for diverting RF energy toward said conductive mesh and away from said at least one electrode.

40. An electrode assembly according to claim 39 wherein said RF energy is induced during an MRI scan.

41. An electrode assembly according to claim 39 wherein the RF energy is substantially diverted at frequencies between approximately 43 MHz to 215 MHz.

42. An electrode assembly according to claim 39 wherein the surface area of said conductive mesh is at least an order of magnitude greater than that of said at least one electrode.

43. An electrode assembly according to claim 42 wherein said high-pass filter comprises at least one capacitor coupled between said conductor mesh and said filer.

44. An electrode assembly according to claim 43 wherein said capacitor has a capacitance in the range of 200 pF to 47,000 pF.

45. An electrode assembly according to claim 44 wherein said conductive mesh is configured to have at least a portion thereof imbedded in said electrode body.

46. An electrode assembly according to claim 42 further comprising a dielectric material disposed between said at least one electrode and said conductive mesh.

47. An electrode assembly according to claim 46 wherein a capacitor plate is coupled between said dielectric material and said conductive mesh.

48. An electrode assembly according to claim 43 further comprising an inductor coupled between said capacitor and said at least one electrode.

49. An electrode assembly for use in a pulse stimulation system configured to be implanted in a patient's body and of the type that includes a pulse generator and a stimulation lead having a proximal end electrically coupled to the pulse generator and having a distal region, the electrode assembly comprising:
- a paddle-shaped electrode body having first and second substantially opposite sides, the body coupled to the distal region of the stimulation lead;
- at least one electrode within said body and electrically coupled to the stimulation lead, said at least one electrode having a first side for delivering therapy to the patient and having a second side; and
- alternating layers of conducting and non-conducting material stacked on said second side to capacitively couple said electrode to the patient's body tissue for diverting RF energy to the patient's body tissue.

50. An electrode assembly according to claim 49 wherein a first one of said alternating layers is in contact with said second side and at least one of said alternating layers is configured for contact with the patient's body tissue.

51. An electrode assembly according to claim 50 wherein said last one is conductive.

52. An electrode assembly according to claim 50 wherein said last one is non-conducting and further comprising a floating electrode coupled to said last one and configured for contact with the patient's body tissue.

53. An electrode assembly according to claim 50 wherein said RF energy is induced during an MRI scan.

54. An electrode assembly according to claim 50 wherein the RF energy is substantially diverted at frequencies between approximately 43 MHz to 215 MHz.

55. An electrode assembly according to claim 52 wherein said floating electrode comprises a conductive mesh.

56. An electrode assembly for use in a pulse stimulation system configured to be implanted in a patient's body and of the type that includes a pulse generator and a stimulation lead having a proximal end electrically coupled to the pulse generator and having a distal region, the electrode assembly comprising:
- a paddle-shaped electrode body having first and second substantially opposite sides, the body coupled to the distal region of the stimulation lead;
- at least one electrode within said body and electrically coupled to the stimulation lead, said electrode having a first side for delivering therapy to the patient, and said electrode having a second side; and
- a layer of dielectric material on said second side and configured to capacitively couple said electrode to the patient's body for diverting RF energy to the patient's body.

57. An electrode assembly according to claim 56 wherein said RF energy is induced during an MRI scan.

58. An electrode assembly according to claim 56 wherein the RF energy is substantially diverted at frequencies between approximately 43 MHz to 215 MHz.

59. An electrode assembly according to claim 56 wherein said dielectric material is a non-conductive polymer.

60. An electrode assembly according to claim 59 wherein said dielectric material is silicone.

61. An electrode assembly according to claim 56 wherein said dielectric material is tantalum oxide.

* * * * *